(12) United States Patent
Andersson (10) Patent No.: US 10,054,539 B2
(45) Date of Patent: Aug. 21, 2018

(54) METHOD FOR DETERMINING A PROPERTY OF A HETEROGENEOUS MEDIUM

(71) Applicant: BTG INSTRUMENTS AB, Säffle (SE)

(72) Inventor: Niclas Andersson, Karlstad (SE)

(73) Assignee: BTG INSTRUMENTS AB, Säffle (SE)

( * ) Notice: Subject to any disclaimer, the term of this patent is extended or adjusted under 35 U.S.C. 154(b) by 144 days.

(21) Appl. No.: 14/872,214

(22) Filed: Oct. 1, 2015

(65) Prior Publication Data

US 2016/0025623 A1    Jan. 28, 2016

Related U.S. Application Data

(63) Continuation of application No. PCT/SE2014/050388, filed on Apr. 2, 2014.

(30) Foreign Application Priority Data

Apr. 2, 2013  (SE) ...................... 1350406

(51) Int. Cl.
*G01N 21/85* (2006.01)
*G01N 21/3577* (2014.01)
(Continued)

(52) U.S. Cl.
CPC ......... *G01N 21/3577* (2013.01); *G01N 15/06* (2013.01); *G01N 21/33* (2013.01);
(Continued)

(58) Field of Classification Search
CPC ........ G01N 15/02; G01N 33/00; G01N 21/85; G01N 21/00; G01N 21/47; G01N 15/06;
(Continued)

(56) References Cited

U.S. PATENT DOCUMENTS 5,245,200 A    9/1993  Fladda
5,619,038 A    4/1997  Parigi et al.
(Continued)

FOREIGN PATENT DOCUMENTS

DE    19613985    11/1997
EP    0340184     11/1989
(Continued)

*Primary Examiner* — Jamil Ahmed
(74) *Attorney, Agent, or Firm* — Gabriela B. Tomescu; Bergenstråhle & Partners AB (57) ABSTRACT

A method of determining a property of a heterogeneous medium in motion comprising at least two phases is provided. A light beam is made small in relation to a part of the medium for which a property is to be determined and the bandwidth of the measurement signal is sufficiently high for distinguishing time periods for the measurement signal which are related to the part of the medium for which a property is to be determined. By using the measurement signal for determining the property of the part of the medium for which a property is to be determined for time periods for the measurement signal which are related to that part of the medium, and determining the property by a mathematical calculation using the measurement signal corresponding to that part of the medium, the properties of individual parts of the medium can be determined.

12 Claims, 6 Drawing Sheets

(51) Int. Cl.
    *G01N 15/06*     (2006.01)
    *G01N 33/34*     (2006.01)
    *G01N 21/33*     (2006.01)
    *G01N 21/47*     (2006.01)
    *G01N 21/49*     (2006.01)

(52) U.S. Cl.
    CPC ......... *G01N 21/4738* (2013.01); *G01N 21/49* (2013.01); *G01N 21/85* (2013.01); *G01N 33/343* (2013.01); *G01N 21/8507* (2013.01); *G01N 2015/0693* (2013.01); *G01N 2201/061* (2013.01)

(58) Field of Classification Search
    CPC ........... G01N 2201/061; G01N 33/343; G01N 21/33; G01N 21/53; G01N 21/4738; G01N 21/3577; G01N 21/8507; G01N 2015/0693; G01N 15/0205; D21C 7/12
    See application file for complete search history.

(56) References Cited

U.S. PATENT DOCUMENTS

2003/0030005 A1\*   2/2003   Karki ..................... D21C 7/12
                                                                                250/373
2004/0011975 A1    1/2004   Nicoli et al.
2006/0087652 A1\*   4/2006   Hardt ................ G01N 15/0205
                                                                                356/338

FOREIGN PATENT DOCUMENTS

| FI | 102015 B | 9/1998 |
|----|----------|--------|
| SE | 464836 | 1/1991 |
| WO | 96/12183 A1 | 4/1996 |

\* cited by examiner

Fig. 7

METHOD FOR DETERMINING A PROPERTY OF A HETEROGENEOUS MEDIUM

This application is a continuation of PCT/SE2014/050388, filed 2 Apr. 2014, which claims priority to Swedish application No. SE-1350406-3 filed 2 Apr. 2013, the entire contents of each of which are hereby incorporated by reference.

TECHNICAL FIELD

The present invention relates generally to a method for determining a property of one or more components or phases in a heterogeneous medium.

BACKGROUND ART

The process efficiency of a pulp mill is a complex function and it depends on for example the pulp type, the pulp properties, the process equipment and the conditions used. For the first process stages in a bleached kraft pulp mill, i.e. cooking, oxygen delignification, and the D0 stage, the challenge is to achieve optimum delignification and high selectivity i.e. obtaining low lignin content and high pulp yield and viscosity. A second challenge is to maximize the pulp production at the required final brightness and strength level.

There is a large impact of operating cooking and oxygen delignification stages properly. Operating too far away from desired working points may result in significant loss of productivity, though sometimes it is very difficult to determine directly and quantitatively, in terms of e.g. pulp yield and strength. From a process control point of view, disturbance factors will contribute to process variability and result in offsets from the target set-points. Such disturbance factors may be related to e.g. raw material, such as chip moisture, liquor strengths, wood composition etc. It may also relate to inaccurate or improper process sensors being used, for example consistency, flow velocity, pH etc. While not every single property and constituent can be measured in every process stage the inherent challenge is to identify the key process parameters, to measure and base process control solutions on those parameters, in order to achieve a high productivity.

The degraded and dissolved lignin residues will ultimately go to the recovery boiler. However some downstream "leakage" will naturally occur and that is the black liquor carryover. Furthermore, even though the majority of the delignification occurs in the cooking stage, still a quite significant Kappa number reduction takes place in subsequent stages and this will add more dissolved lignin to the process streams.

This black liquor carryover, referring both to organic and inorganic constituents, is well known concerning its composition, and there are sensor technologies used today that try to capture the carryover. However they do not measure specifically the dissolved lignin content which has been identified being the most critical parameter in pulp washing but rather the content of inorganic matter in the black liquor.

The lignin content in the process fluid can be determined by measuring the absorption of preferably ultra violet (UV) light. However, this implies that the fibres have been separated and can thus be applied on-line only on a relatively pure fluid flow, i.e., with no fibres. Some compensation for the fibre content (including fibre fragments and other light scattering particles) can be achieved by performing the measurement at two or more wavelengths, but even at relatively low fibre contents these fibres block almost all light when measuring for example the light transmittance whereby the determination of the fluid phase will be interfered or made impossible.

The patent document SE 464 836 describes that due to the low number of large particles, such as fibres, present in a given small measuring volume it will statistically be occasions when there will be no large particles in this volume, provided that the concentration is sufficiently low relatively to the volume. However, the number of small particles is high also in a small volume, such as 1 mm$^3$, and statistically the concentration of small particles will remain essentially constant over time.

Figure 1:
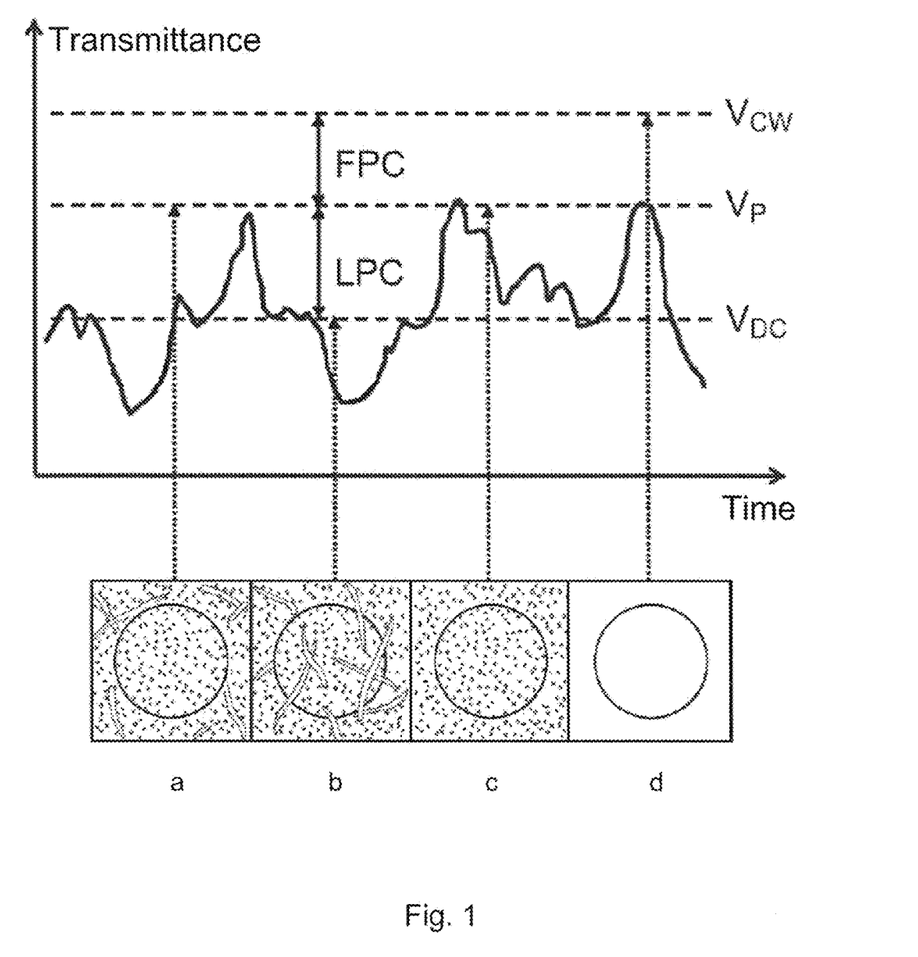
FIG. 1 shows an explanatory sketch for measuring transmittance with high frequency used today.

FIG. 1 shows an explanatory sketch for measurement of transmittance with a high frequency, with a small measuring volume containing a suspension with both large and small particles. The graph shows signal level as a function of time, wherein $V_{CW}$ is the signal level for pure water, $V_P$ is the top level of the signal and $V_{DC}$ is the average signal level. FPC corresponds to the concentration of small particles and LPC corresponds to the concentration of large particles.

When measuring the light attenuation, or inversely transmittance, when the medium flows through a given measuring volume, the signal level will be the highest when there are no large particles in the measuring volume, i.e., the top level, see illustration d) in FIG. 1, and correspond to the concentration of small particles, see illustrations a) and c) in FIG. 1. The average signal level is influenced by both large and small particles, see illustration b) in FIG. 1, which means that the concentration of large particles can be determined from the average signal level together with the top level, calculated in a suitable way. The method is graphically described in FIG. 1, which thus is general and applies for measurement of light attenuation, i.e., transmittance, although it in principle can be applied also when measuring reflectance.

By using a small measuring volume and a high time resolution, a differentiation between large and small particles is made possible. It is thus an advantage that the disproportionally large contribution of the large and small particles to the measuring signal can be compensated for and that the concentration of both large and small particles, and also the total particle concentration, can be obtained.

However, determining the properties of individual phases in a heterogeneous medium remains a problem.

SUMMARY OF INVENTION

An object of the present invention is to provide a method of determining a property of respective parts or components of a heterogeneous medium.

The invention is based on the insight that a property of a part of a heterogeneous medium can be calculated by using a small measuring volume and high signal bandwidth, in combination with applying mathematical models.

According to the invention there is provided a method of determining a property of a heterogeneous medium in motion comprising at least two phases, the method comprising the following steps: irradiating the medium with a light beam having at least one predetermined wavelength, obtaining a measurement signal representative for detected light leaving the medium, wherein the light beam is small in relation to a part of the medium for which a property is to be determined, and wherein the bandwidth of the measurement signal is sufficiently high for distinguishing time periods for the measurement signal which are related to the part of the medium for which a property is to be determined, wherein the method is characterized by the following step: for time periods for the measurement signal which are related to the part of the medium for which a property is to be determined, using the measurement signal for determining the property of the part of the medium for which a property is to be determined, and wherein the property to be determined is determined by a mathematical calculation using the measurement signal corresponding to the part of the medium for which a property is to be determined. The properties of individual parts of the medium can thereby be determined.

In a preferred embodiment, the property to be determined is any of the following: a chemical composition, brightness, and colour.

In a preferred embodiment, the part of the medium for which a property is to be determined is the liquid phase of a fibre suspension.

In a preferred embodiment, the property to be determined is the concentration of dissolved lignin. The wavelength of the measurement signal is then preferably in the UV range and preferably essentially at 280 nm. The measurement can preferably be made by combining a measurement of UV light within the absorption range of lignin and infrared (IR) light in a wavelength range without influence from chemical composition In a preferred embodiment, the part of the medium for which a property is to be determined is fibre material, preferably during refining of wooden chips to pulp. The property to be determined can then be the moisture content in the fibre material.

In a preferred embodiment, the method comprises the step of calibration by means of a multivariate calibration technique, preferably Partial Least Squares or Projection to Latent Structures, In a preferred embodiment, measuring data for more than one wavelength or wavelength bands is combined.

In a preferred embodiment, a measuring volume is used which is 0.05-1000 $mm^3$, and preferably about 1 $mm^3$.

In a preferred embodiment, the bandwidth of the measurement signal is 0.05-10 KHz, and preferably at least 1 kHz.

BRIEF DESCRIPTION OF DRAWINGS

The invention is now described, by way of example, with reference to the accompanying drawings, in which.

DESCRIPTION OF EMBODIMENTS

In the following, a detailed description of a method of determining a property of a heterogeneous medium will be described.

In this description, the term "heterogeneous medium" is intended to define a heterogeneous medium having two or more phases, such as a suspension with fibres or other particles. The term "heterogeneous medium in motion" is intended to define a heterogeneous medium which is conveyed in for example a pipe. An example is a suspension in a pipe, parts of chips measured in a chute, material on a conveyor belt etc.

With the definition "the light beam is small in relation to" is intended to describe that the size or diameter of the light beam is directly related to the measuring volume, i.e., the size of the light beam depends on the size of the part to be measured, such as particle size or the size of the gap between particles. The requirements on the bandwidth, i.e., the time resolution, also depend on this but also on the flow rate of the medium.

The term "on-line" is intended to describe that the measuring is performed either directly in the process line, sometimes also called "in-line", or in another way, such as a sub-flow which is automatically taken from the process and is allowed to flow or be pumped past a probe. The on-line measuring is typically performed continuously or essentially continuously relatively to the dynamics of the process.

The terms "phases" and "components" describe the different constituents of the medium, such as particles, fibres, liquids and gas.

The term "pipe" usually refers to a process pipe, but can also include a conveyor or a tube etc., depending on the application.

Figure 2:
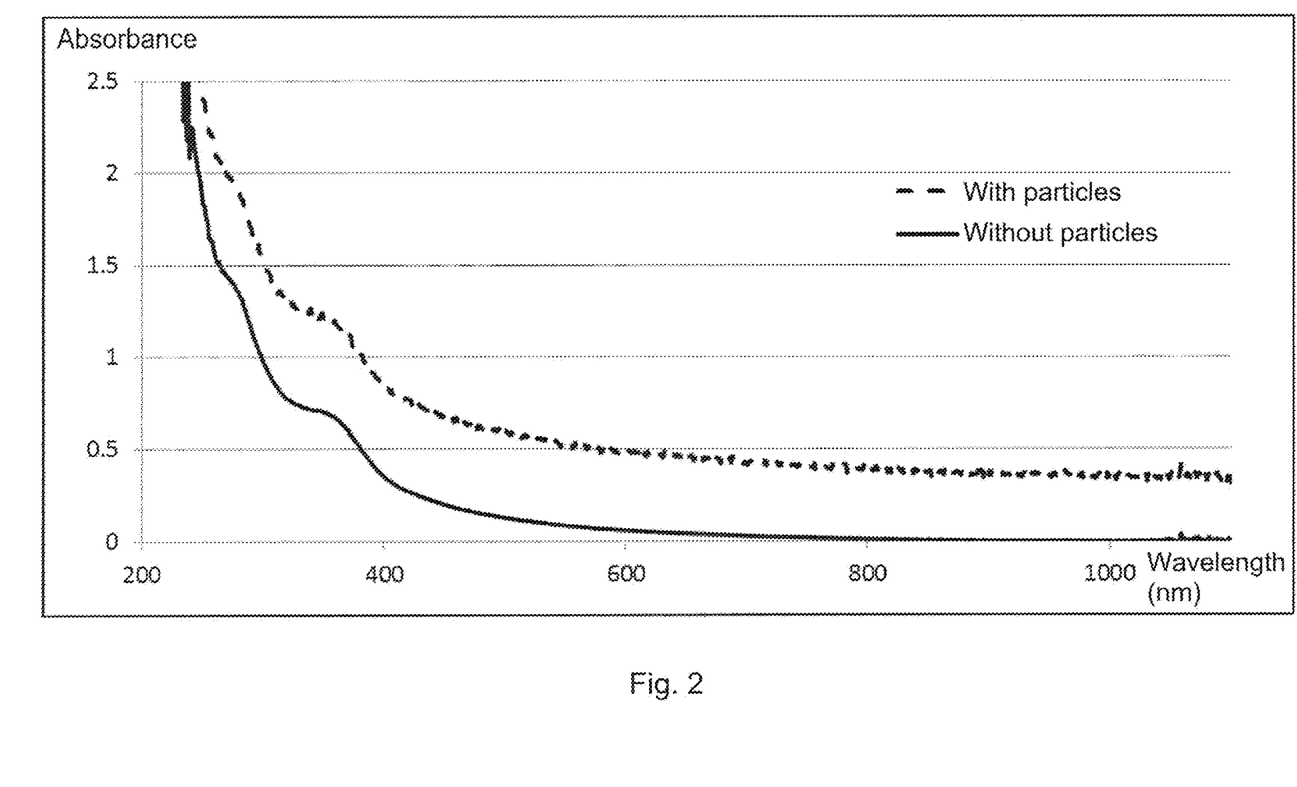
FIG. 2 shows an absorbance spectrum on a bleach filtrate.

FIG. 2 shows spectra, i.e., absorbance as a function of wavelength for a bleaching filtrate with particles, such as fines (dashed line) and without particles (solid line).

In a first embodiment the method according to the invention is used for determining a property of the liquid phase of a fibre suspension, preferably the concentration of dissolved lignin. The strong light absorption of the lignin molecule in the UV-VIS (ultraviolet and visible) region is, due to its aromatic structure, well known and it is employed in currently used technology for automatic fiber lignin content measurement typically expressed as Kappa number. It can also be used for the determination of dissolved lignin by light transmittance measurement. Since such a measurement can only be performed without fibres present in the measuring volume, using a small measuring volume, the time periods corresponding to measurement of only the filtrate portion can be identified and used to calculate the light transmittance and absorbance, and subsequently to determine the dissolved lignin concentration.

For this application the value of FPC in FIG. 1 is used, measured at a wavelength in the UV range and preferably at 280 nm in order to measure the concentration of dissolved lignin. Also a higher wave length, i.e., in the visible range, can be used if the concentration of lignin is high enough to give sufficient absorbance for a good determination of the concentration.

A suitable measuring volume in this application is about 1 $mm^3$ with a measuring frequency, i.e., bandwidth of at least about 1 kHz.

In the case the concentration of fibre fragments is relatively high, which means that they are present in a relatively large number and statistically are present in a constant concentration also in the limited measuring volume used, the measurement can preferably be made by combining a measurement of UV light within the absorption range of lignin and infrared (IR) light in a wavelength range without influence from the chemical composition The latter can be regarded as a compensation for light scattering and light blocking due to fibre fragments and that some large fibres nevertheless are present, i.e., that the top level of the signal does not represent a condition with no fibres present in the measuring volume. As can be seen in FIG. 2, the influence of this light scattering can be significant and is seen as an increased absorbance across the entire range of wavelengths in the presence of small light-scattering particles, such as fibre fragments.

Figure 3:
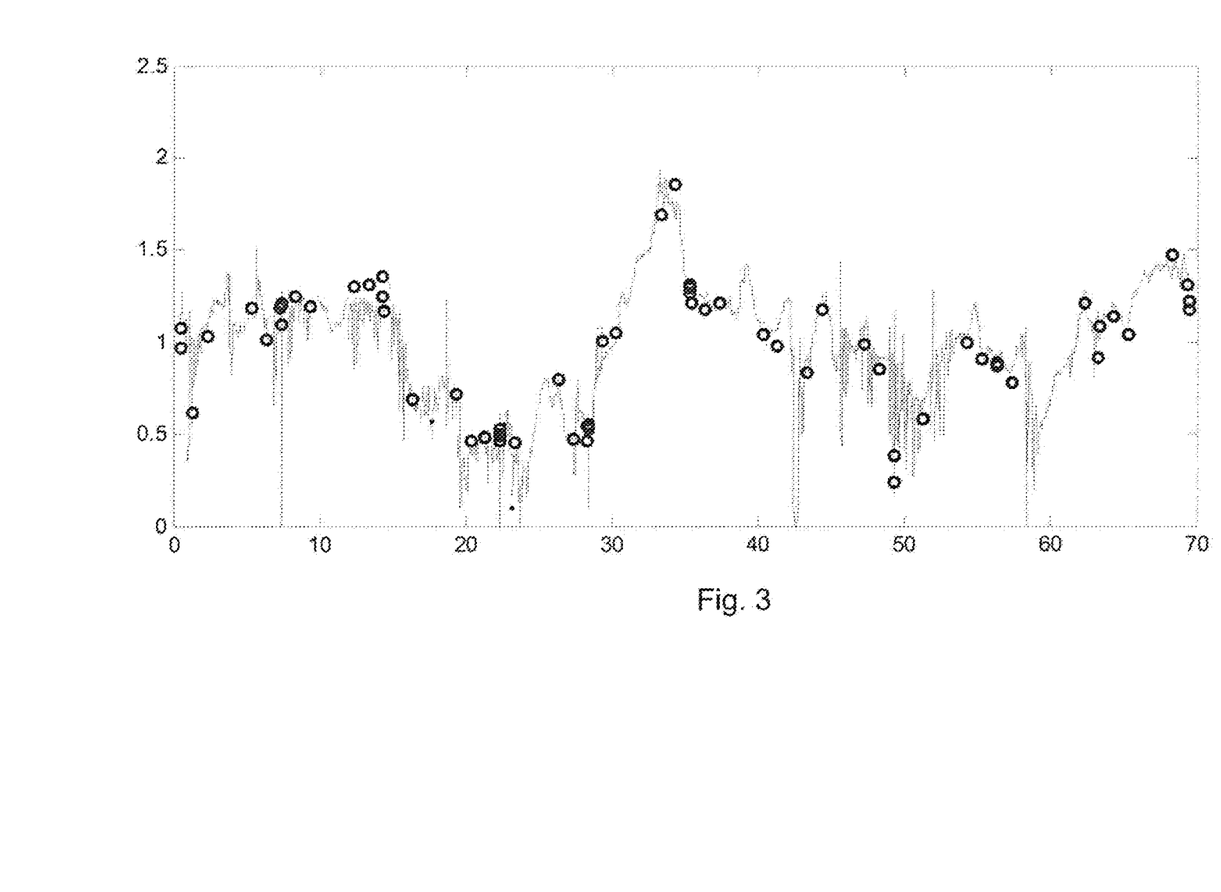
FIG. 3 is a diagram showing data from an on-line application of the present invention.
Figure 4:
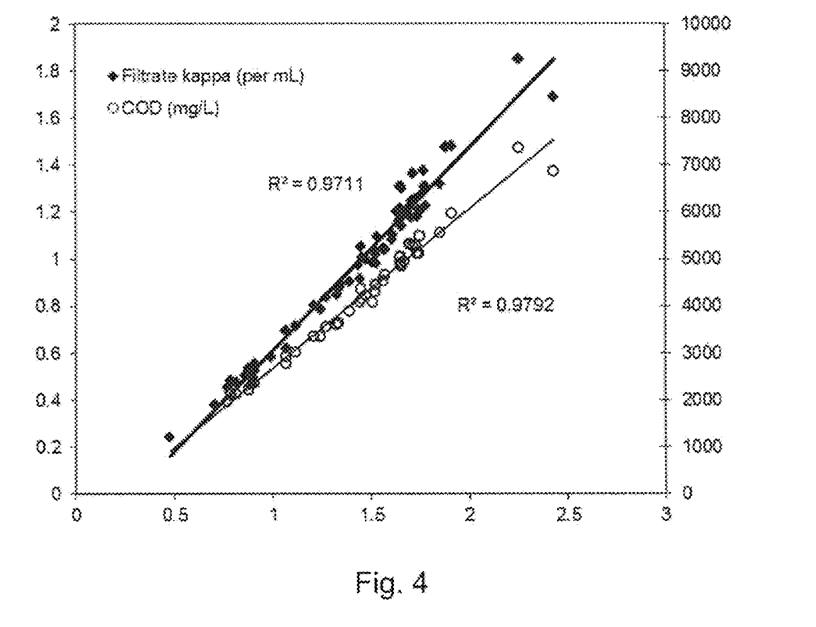
FIG. 4 is a diagram of filtrate Kappa number and COD vs. sensor raw signal.

FIG. 3 shows data from an on-line application of the method according to the invention wherein both the concentration of fibres and that of lignin vary over time. An inline sensor was installed before a wash press prior to the D0 stage of a softwood kraft pulp mill, at a pulp consistency of 4-5%. FIG. 3 trends the sensor output during a period of 70 days, scaled to filtrate Kappa number, i.e., the permanganate consumption of the filtrate, along with laboratory reference data (circles—69 samples). Obviously the fit between the sensor trend and the reference data is very good. This is also seen in FIG. 4, showing both filtrate Kappa number and COD vs. the sensor's raw signal, both with correlation coefficients r2 above 0.97. The variability of the dissolved lignin concentration is also quite remarkable.

In a second embodiment of the invention the method is used for determining the moisture content in fibre material during refining of wooden chips to pulp, so called mechanical pulp. The moisture content is an important control parameter in order to minimize the energy consumption and to achieve the desired fibre and paper properties, for example.

Figure 5A:
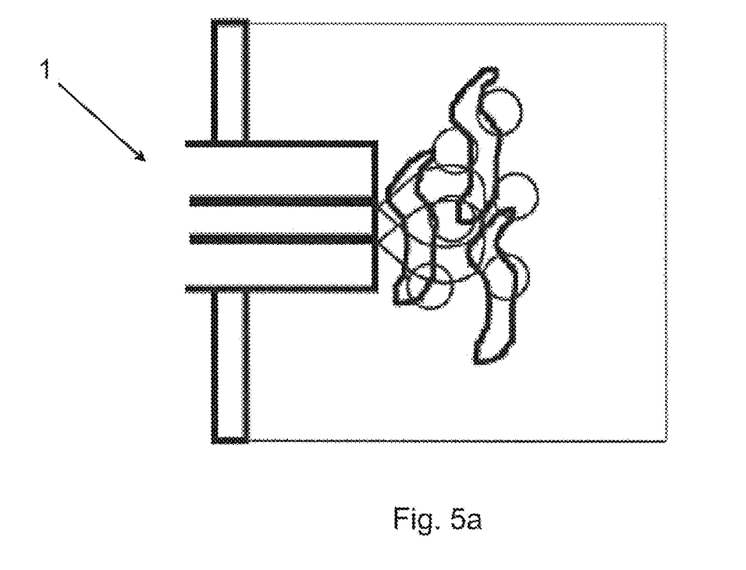
FIGS. 5a and 5b are explanatory sketches of a probe for measuring reflectance by means of fibre optics.
Figure 5B:
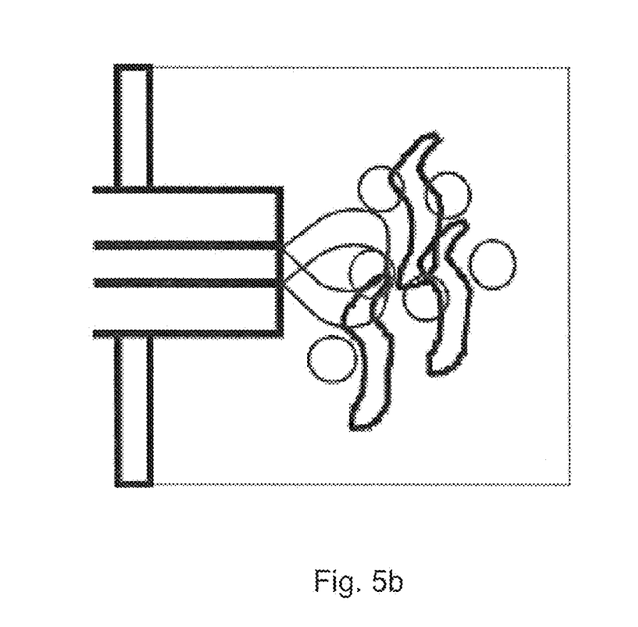

FIGS. 5a and 5b show an example wherein the measuring volume of a probe, generally designated 1, is determined by an optical fibre irradiating a medium and an optical fibre collecting the reflected light for detection. With a heterogeneous medium there will occasionally be material with the measuring volume closest to the probe, in the present example closer to the ends of the optical fibres, see FIG. 5a, which gives a generally higher reflection signal across the range of wavelengths. At other times there will be no particles within the measuring volume closest to the probe 1, see FIG. 5b, but instead more water vapour, which gives a low reflection signal. The measured spectrum is thus valid for the average composition in the measuring volume for the time of measuring. In the present example this means that also the gas phase, the water vapour and its temperature etc. will to a large extent influence the spectrum, as well as the total amount or concentration of fibre material in the measuring volume, as indicated above.

Figure 6:
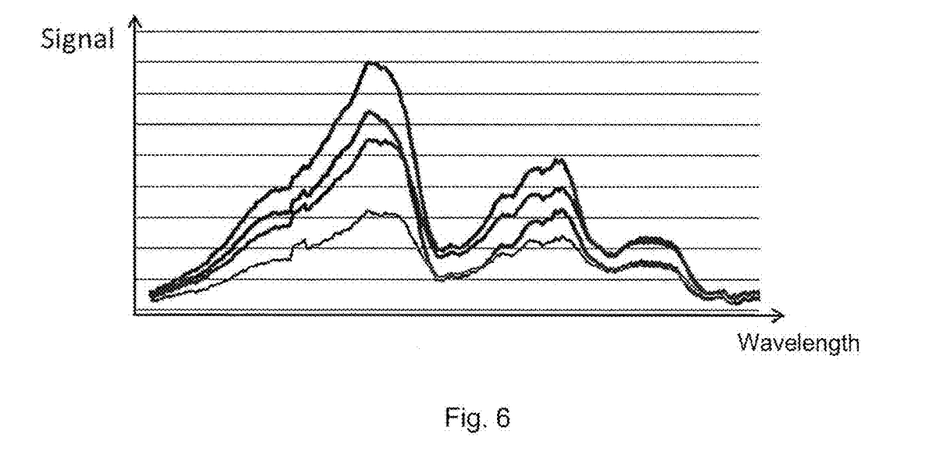
FIG. 6 shows a reflection spectrum in the near infrared area for samples with different distances from the probe during measuring.

FIG. 6 shows reflection spectra within the near infrared (NIR) wavelength range for samples with different distances from the probe during measuring. The samples are measured in a laboratory environment on the same sample but at different, determined distances from the probe. The curve with the highest signal corresponds to the sample which is closest to the probe and a greater distance generally gives a lower measurement signal. However, it will be appreciated that the shapes of the spectra are not totally identical for the different distances, which is at least partly due to water vapour between the sample and the probe which influences the signal in different ways at different wavelengths and to different extents depending on the distance between the sample and the probe.

In order to achieve sufficient accuracy and precision during the determination of properties a large part of the light spectra must be measured, usually by means of a spectrophotometer, and using some kind of multivariate calibration technique, for example Partial Least Squares or Projection to Latent Structures (PLS), which consequently also requires a relatively large number of reference samples for calibration.

Figure 7:
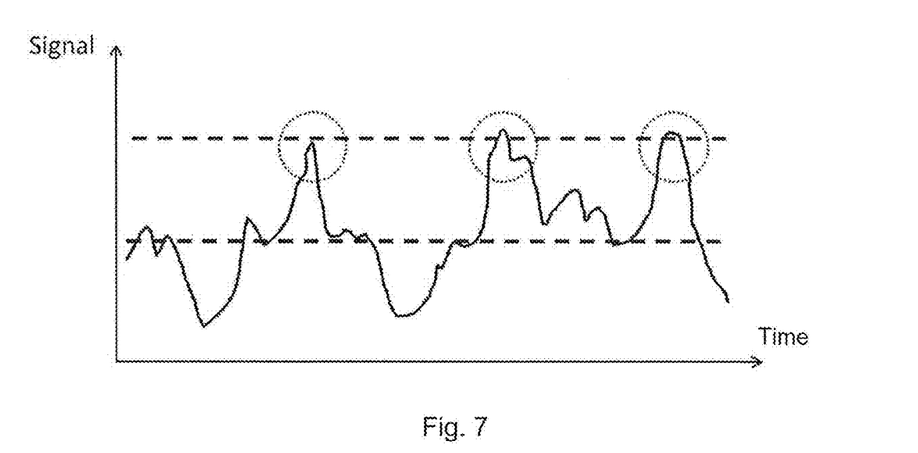
FIG. 7 shows a diagram of a signal measured at a given wavelength as a function of time.

FIG. 7 shows a diagram corresponding to the curve shown in FIG. 1. FIG. 7 shows the principle for the signal measured at a given wavelength alternatively to the average signal across a predetermined wavelength range as a function of time. The measurement frequency and the size of the measuring volume in relation to the size distribution of the different phases of the medium and the flow rate are in this example sufficient so that the highest signal level which occasionally appears, marked with circles in the figure, corresponds to measuring on material very close to the probe, see FIG. 5a.

By combining measuring data for more than one wavelength or wavelength bands for these particular time periods the properties of the fibre material can be determined in an easier way and with higher accuracy. It is preferred that the measuring is performed simultaneously in order to achieve the best possible synchronization between the different wavelengths. However, it is also possible to measure the representative time periods for the different wavelengths individually and then combine them.

Preferred embodiments of a method of determining a property of a heterogeneous medium have been described. It will be appreciated that these can be varied within the scope of the appended claims without departing from the inventive idea.

The invention claimed is:

1. A method of determining a property of a phase of a heterogeneous medium in motion comprising at least two phases, the method comprising the following steps:
   irradiating the medium with a light beam having at least one predetermined wavelength,
   obtaining a measurement signal representative for detected light leaving the medium,
   wherein
   the light beam is small in relation to the phase of the medium for which a property is to be determined,
   the bandwidth of the measurement signal is sufficiently high for distinguishing time periods for the measurement signal which are related to the phase of the medium for which a property is to be determined,
   for time periods for the measurement signal which are related to the phase of the medium for which a property is to be determined, using the measurement signal for determining the property of the phase of the medium for which a property is to be determined, and
   the property to be determined is determined by a mathematical calculation using the measurement signal corresponding to the phase of the medium for which a property is to be determined.

2. The method according to claim 1, wherein the property to be determined is any of the following: a chemical composition, brightness, and colour.

3. The method according to claim 1, the phase of the medium for which a property is to be determined is the liquid phase of a fibre suspension.

4. The method according to claim 3, wherein the property to be determined is the concentration of dissolved lignin.

5. The method according to claim 3, wherein the wavelength of the measurement signal is in the UV range and preferably essentially at 280 nm.

6. The method according to a claim 3, wherein the measurement can preferably be made by combining a measurement of UV light within the absorption range of lignin and infrared (IR) light in a wavelength range without influence of chemical composition.

7. The method according to claim 1, wherein the phase of the medium for which a property is to be determined is fibre material, preferably during refining of wooden chips to pulp.

8. The method according to claim 7, wherein the property to be determined is the moisture content in the fibre material.

9. The method according to claim 1, comprising the step of calibration by means of a multivariate calibration technique, preferably Partial Least Squares or Projection to Latent Structures.

10. The method according to claim 1, wherein measuring data for more than one wavelength or wavelength bands is combined.

11. The method according to claim 1, wherein a measuring volume is used which is 0.05-1000 mm$^3$, and preferably about 1 mm$^3$.

12. The method according to claim 1, wherein the bandwidth of the measurement signal is 0.05-10 kHz, and preferably at least 1 kHz.

* * * * *